(12) United States Patent
Swiss et al.

(10) Patent No.: US 9,115,066 B2
(45) Date of Patent: Aug. 25, 2015

(54) TRISUBSTITUTED METHYL ALCOHOLS AND THEIR POLYMERIZABLE DERIVATIVES

(71) Applicant: Indicator Systems International, Inc., Newport Beach, CA (US)

(72) Inventors: Gerald F. Swiss, Rancho Santa Fe, CA (US); Photon Rao, Foster City, CA (US); Ram W. Sabnis, Atlanta, GA (US)

(73) Assignee: Indicator Systems International, Inc., Newport Beach, CA (US)

( * ) Notice: Subject to any disclaimer, the term of this patent is extended or adjusted under 35 U.S.C. 154(b) by 0 days.

(21) Appl. No.: 13/715,014

(22) Filed: Dec. 14, 2012

(65) Prior Publication Data

US 2013/0197262 A1    Aug. 1, 2013

Related U.S. Application Data

(60) Provisional application No. 61/570,626, filed on Dec. 14, 2011, provisional application No. 61/698,427, filed on Sep. 7, 2012.

(51) Int. Cl.

| | |
|---|---|
| *C07C 43/23* | (2006.01) |
| *C07C 69/738* | (2006.01) |
| *C07C 265/08* | (2006.01) |
| *C07C 331/24* | (2006.01) |
| *C07C 69/54* | (2006.01) |

(52) U.S. Cl.
CPC ............. *C07C 43/23* (2013.01); *C07C 69/54* (2013.01); *C07C 69/738* (2013.01); *C07C 265/08* (2013.01); *C07C 331/24* (2013.01)

(58) Field of Classification Search
CPC ............................ C07C 43/23; C07C 265/08
See application file for complete search history.

(56) References Cited

U.S. PATENT DOCUMENTS

| | | | |
|---|---|---|---|
| 4,079,038 A | 3/1978 | Choi et al. | |
| 4,093,709 A | 6/1978 | Choi et al. | |
| 4,138,344 A | 2/1979 | Choi et al. | |
| 4,938,763 A | 7/1990 | Dunn et al. | |
| 5,181,905 A | 1/1993 | Flam | |
| 5,939,598 A | 8/1999 | Kucherlapati et al. | |
| 6,140,503 A * | 10/2000 | Lin et al. ............. | 546/255 |
| 6,640,130 B1 | 10/2003 | Freeman et al. | |
| 7,056,901 B2 | 6/2006 | Frechet et al. | |
| 7,531,633 B2 | 5/2009 | Pavliak et al. | |
| 8,425,996 B2 | 4/2013 | Gorski et al. | |
| 2004/0241214 A1 | 12/2004 | Kirkwood et al. | |
| 2006/0034726 A1 | 2/2006 | Sunshine et al. | |
| 2010/0178203 A1 | 7/2010 | Kane et al. | |
| 2010/0196636 A1 | 8/2010 | Gorski et al. | |
| 2011/0104261 A1 | 5/2011 | Drummond et al. | |
| 2013/0022997 A1 | 1/2013 | Huang et al. | |
| 2013/0064772 A1 | 3/2013 | Swiss et al. | |

FOREIGN PATENT DOCUMENTS

| | | |
|---|---|---|
| EP | 1 506 959 A2 | 2/2005 |
| WO | WO-01/72926 A1 | 10/2001 |
| WO | WO-2005/057207 A1 | 6/2005 |
| WO | WO-2006/032893 A2 | 3/2006 |
| WO | WO-2008/127411 A1 | 10/2008 |
| WO | WO-2010/085755 A1 | 7/2010 |
| WO | WO-2013/036771 A1 | 3/2013 |
| WO | WO-2013/090682 A1 | 6/2013 |

OTHER PUBLICATIONS

Lambert et al. Analyst (Cambridge, United Kingdom), 1981, 106(1266), 1013-1016.*
Desjardins et al. Journal of Soil Contamination (1999), 8(2), 175-195.*
Lifschitz, Recueil des Travaux Chimiques des Pays-Bas et de la Belgique (1934), 53, 191-196.*
Witting et al. Berichte der Deutschen Chemischen Gesellschaft [Abteilung] B: Abhandlungen (1938), 71B, 1903-12.*
PCT International Search Report and Written Opinion dated Apr. 29, 2013 in related PCT Patent Application No. PCT/US2012/069686.
Amanlou, et al., "Magnetic resonance contrast media sensing in vivo molecular imaging agents: an overview", Current Radiopharmaceuticals, (2011), 4(1):31-43.
Drummond, et al., "Current status of pH-sensitive liposomes in drug delivery," Progress in Lipid Research, (2000), 39:409-460.
Edlund, et al., "Degradable Polymer Microspheres for Controlled Drug Delivery," Advances in Polymer Science, (2002), 157:67-112.
Feldman, et al., "Breast implant infections: is cefazolin enough?", Plast Reconstr Surg. (2010)126(3):779-85.
Gemmel, et al. "Prosthetic joint infections: radionuclide state-of-the-art imaging", Eur J Nucl Med Mol Imaging,(2012),39(5):892013909.
International Search Report and Written Opinion dated Jan. 25, 2013 in related PCT Application No. PCT/US12/54171.
Kayaki, et al., "A Highly Effective (Triphenyl phosphite)palladium Catalyst for a Cross-Coupling Reaction of Allylic Alcohols with Organoboronic Acids", European Journal of Organic Chemistry, (2004), Issue 24, pp. 4989-4993.
Kono, et al., "Temperature-Sensitive Liposomes", Methods in Enzymology, (2004), 387:73-82.
Lee, et al., "Controlling Degradation of Acid-Hydrolyzable Pluronic Hydrogels by Physical Entrapment of Poly(lactic acid-co-glycolic acid) Microspheres," Macromolecular Bioscience, (2004), 4:957-962.
Mino et al., "Room-Temperature Palladium-Catalyzed Allyl Cross-Coupling Reaction with Boronic Acids Using Phosphine-Free Hydrazone Ligands", Synlett, 2008, 2008(17):2711-2715.
Tang, et al., "Block copolymer micelles with acid-labile ortho ester side-chains: Synthesis, characterization, and enhanced drup delivery to human glioma cells," J. Control Release, (2011), 151(1):18-27.
Ueda et al., "A Transition-Metal-Free Cross-Coupling Reaction of Allylic Bromides with Aryl- and Vinylboronic Acids", Synlett, 2012, 23(07):1085-1089.
Van Der Heyden, et al., "Protein encapsulation and release from degradable sugar based hydrogels," European Polymer Journal, (2009), 45(6):1689-1697.

(Continued)

*Primary Examiner* — Yong Chu
*Assistant Examiner* — Ana Z Muresan
(74) *Attorney, Agent, or Firm* — Foley & Lardner, LLP

(57) ABSTRACT

Provided herein are trisubstituted methyl alcohols, preferably pH indicators that are substituted with optionally substituted aryl and or optionally substituted heteroaryl groups, and optionally include one or more polymerizable substituents.

2 Claims, No Drawings

(56) References Cited

OTHER PUBLICATIONS

Wang, et al., "Nickel-Catalyzed Reductive Coupling of Aryl Halides with Secondary Alkyl Bromides and Allylic Acetate", Org. Lett., (2012), 14(13):3352-5.

Yu, et al., "pH-sensitivity of swelling of polyurethane crosslinked polyacrylate network," Polymer Bulletin, (1993), 30:719-724.

Yuan, et al., "PEG-detachable and acid-labile cross-linked micelles based on orthoester linked graft copolymer for paclitaxel release," Nanotechnology, (2011), 22(33):335601 (p. 1-10).

* cited by examiner

US 9,115,066 B2

TRISUBSTITUTED METHYL ALCOHOLS AND THEIR POLYMERIZABLE DERIVATIVES

CROSS REFERENCE TO RELATED APPLICATIONS

This application claims priority to U.S. provisional application Ser. No. 61/570,626, filed Dec. 14, 2011, and Ser. No. 61/698,427, filed Sep. 7, 2012. These applications are hereby incorporated by reference in their entireties.

FIELD OF THE INVENTION

This invention relates to trisubstituted methyl alcohols that are substituted with optionally substituted aryl and or optionally substituted heteroaryl groups, which preferably act as pH indicators. This invention also relates to such trisubstituted methyl alcohols that contain one or more polymerizable functional groups so as to participate with polymerizable monomers in polymer formation.

BACKGROUND OF THE INVENTION

Triarylmethyl indicator compounds that detect the presence of acidic molecules are useful, for example to detect the presence of bacteria in foods, wounds, and the like. To detect bacterial growth, the indicator is included in a polymeric matrix that contacts, for example, the wound or the food. If the indicator is not covalently bound to the polymeric matrix, there is a possibility that the indictor can leach out of the polymeric matrix and mix with the food or wound. While this problem can be addressed by cross-linking the polymer to entrap the indicator, there are many examples where the polymers are not desirably cross-linked. Moreover, cross-linking is not an absolute assurance that a small amount of the indicator will still not leach.

Hexamethoxy red and heptamethoxy red are preferred pH indicators as they are transparent at pH's of about 6 and above, and bright red/purple at lower pHs. The use of such indicators is beneficial as it provides an accurate visual analysis of the presence of bacterial growth. While there exists numerous ways to modify pH indicators to include a polymerizable group, it is essential that such modification does not significantly alter the pKa of the so modified indicator so that the indicator retains its underlying detection characteristics. Provided here are triarylmethyl indicators which can detect a wide range of acidity, and/or that comprise one or more polymerizable groups. These polymerizable groups are introduced in such a manner that the pKa of these indicators is not materially altered.

SUMMARY OF THE INVENTION

Provided herein are novel trisubstituted methyl alcohols of Formula A:

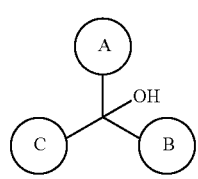

(A)

wherein each of ring A, ring B, and ring C independently represent an aryl or a heteroaryl optionally substituted with substituents as defined herein, for example, in Formulas (I) and (II), with the proviso that a compound of Formula (A) excludes pentamethoxy red, hexamethoxy red, or heptamethoxy red. Preferred aryl groups include phenyl and naphthyl. Preferred heteroaryl groups include furanyl, benzofuranyl, thiophenyl, benzothiophenyl and such other electron rich, neutral (i.e., neither basic nor alkaline) heteroaryls. Preferred compounds of Formula (A) are neutral, as defined above. More preferred compounds of Formula (A) are those that undergo a protonation and removal of the hydroxy group, and a concomitant generation of colored cation at a pH of 4.5 to 6:

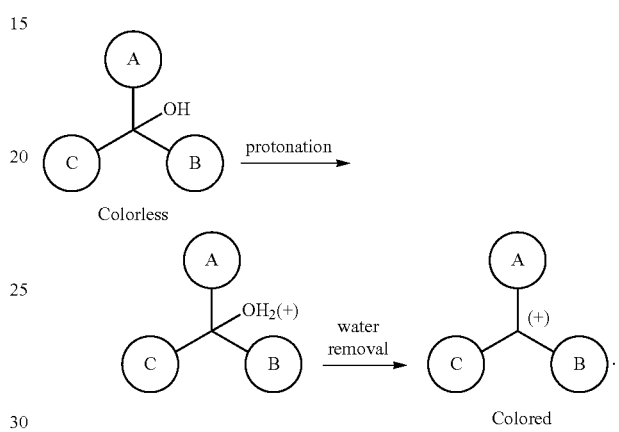

In certain aspects, all three rings of Formula (A) are aryl. In certain other aspects, two of the rings of Formula (A) are aryl. In certain other aspects, one of the rings of Formula (A) are aryl. In certain other aspects, none of the rings of Formula (A) are aryl.

In one aspect, provided herein are compounds of Formulas (I) and (II):

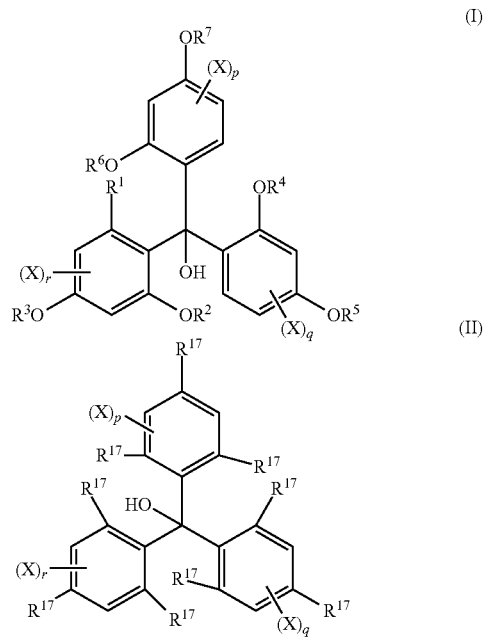

wherein
each of p, q, and r independently are, 0, 1, or 2, provided that the compound of Formula (II) excludes pentamethoxy red, hexamethoxy red, and heptamethoxy red;

each X independently is a substituent that is:
  $C_1$-$C_6$ alkyl, optionally substituted with 1-3 phenyl, oxo, cyano, halo, nitro;
  vinyl optionally substituted with 1-3 $C_1$-$C_6$ alkyl, phenyl, or naphthyl, wherein the phenyl or naphthyl is substituted with 1-3 $C_1$-$C_6$ alkoxy, cyano, halo, or nitro;
  ethynyl optionally substituted with 1-3 $C_1$-$C_6$ alkyl, phenyl, or naphthyl, wherein the phenyl or naphthyl is substituted with 1-3 $C_1$-$C_6$ alkoxy, cyano, halo, or nitro;
  —$COR^{30}$, wherein $R^{30}$ is hydrogen, $C_1$-$C_6$ alkyl, phenyl, napthyl, or an oxime thereof;
  phenyl or naphthyl, preferably phenyl, optionally substituted with 1-4, preferably 1-3, more preferably 1-2, and still more preferably 1 substituent, wherein the substituent is selected from the group consisting of alkyl, preferably $C_1$-$C_6$ alkyl, —$OR^{18}$, wherein $R^{18}$ is alkyl, preferably $C_1$-$C_6$ alkyl, $C_3$-$C_8$ cycloalkyl, $C_6$-$C_{10}$ aryl, preferably phenyl, each of which are optionally substituted with 1-5, preferably, 1-3 substituents selected from the group consisting of halo, preferably fluoro, cyano, $C_1$-$C_6$ alkoxy, and aryloxy; —$OR^{19}$, wherein $R^{19}$ is hydrogen, $C_1$-$C_6$ alkyl, $C_3$-$C_8$ cycloalkyl, or phenyl, each of which are optionally substituted with 1-5, preferably, 1-3 substituents selected from the group consisting of halo, preferably fluoro, cyano, nitro, $C_1$-$C_6$ alkoxy, and aryloxy, or $R^{19}$ is Pg; or cyano, halo, nitro;
Pg is a hydroxyl protecting group;
each $R^{17}$ independently is hydrogen or X, wherein X is defined as above;
$R^1$ is hydrogen, X, or —$OR^8$, wherein X is defined as above;
each of $R^2$-$R^8$ independently is hydrogen, Pg, $C_1$-$C_4$ alkyl or is -L-$R^9$;
$R^9$ is a polymerizable group;
L is a covalent bond or a linker which joins the one or more polymerizable groups to the oxygen atom to which it is attached;
provided that for Formula (II), if p+q+r=0, then at least one, preferably 2, more preferably 3, still more preferably 4, and yet more preferably 5 of $R^{17}$ groups are X.

In one embodiment, the compound provided is of Formula (I-A):

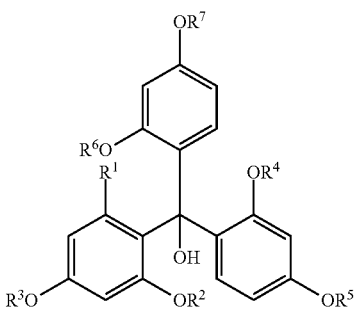

(I-A)

wherein
  $R^1$ is hydrogen, —OH, —OPg or —$OR^8$;
  each of $R^2$-$R^8$ independently is hydrogen, Pg, $C_1$-$C_4$ alkyl or is -L-$R^9$ provided that at least one of $R^2$-$R^8$ is -L-$R^9$; and
  $R^9$, Pg, and L are defined as above.

Within the aspects and embodiments provided herein, in one embodiment, $R^1$ is —$OR^8$, and each of $R^2$-$R^8$ independently is Pg, $C_1$-$C_4$ alkyl or -L-$R^9$, provided that at least one of $R^2$-$R^8$ is -L-$R^9$. In another embodiment, at least one of $R^2$-$R^8$ is hydrogen or $R^1$ is —OH. In a preferred embodiment, p+q+r is 3, more preferably, p+q+r is 2, and yet more preferably, p+q+r is 1.

In yet another preferred embodiment, provided herein is a compound of Formula (II), of Formula (I-B):

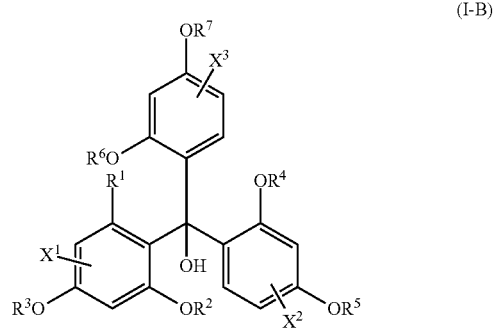

(I-B)

where $X^1$-$X^3$ are independently hydrogen or are defined as X in Formula (I), and $R^1$-$R^7$ are defined as in Formula (I).

In yet another preferred embodiment, provided herein is a compound of Formula (II), of Formula (II-A):

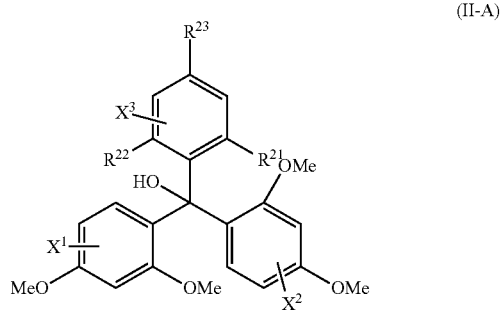

(II-A)

where $X^1$-$X^3$ are independently hydrogen or are defined as X in Formula (I), and $R^{21}$-$R^{23}$ are independently hydrogen or defined as X in Formula (I).

As used herein, a polymerizable group preferably refers to a group that includes a vinyl moiety that is polymerized under various well known condition with monomers containing a vinyl moiety. A polymerizable group also includes a moiety that can react with an electrophile or a nucleophile, preferably readily, to form a covalent linkage. Non-limiting examples include, —N=C=O, N=C=S, $CO_2Ar_F$, azide, ethynyl, and the like. As used herein $Ar_F$ refers to a pentafluoro or tetrafluoro phenyl group. Leaving groups other than —$OAr_F$ are well known to the skilled artisan and useful herein, and will be apparent to the skilled artisan upon reading this disclosure. Other polymerizable groups are well known to the skilled artisan and will be apparent to them upon reading this disclosure.

Also provided herein are polymers which contain trisubstituted methyl alcohol indicator covalently bound to the polymer wherein sufficient indicator is bound to the polymer such that the color of the polymer is changed from transparent at neutral pH to colored at acidic pH.

DETAILED DESCRIPTION OF THE INVENTION

This invention relates to trisubstituted methyl alcohols and polymerizable forms thereof. Before describing this invention in detail the following terms are defined.

DEFINITIONS

"Alkyl" refers to monovalent saturated aliphatic hydrocarbyl groups having from 1 to 10 carbon atoms and, in some embodiments, from 1 to 6 carbon atoms. This term includes, by way of example, linear and branched hydrocarbyl groups such as methyl, ethyl, n-propyl, isopropyl, n-butyl, isobutyl, sec-butyl, t-butyl, n-pentyl, and neopentyl.

"$C_x$—$C_y$" with respect to a group refers to that group having from x to y carbon atoms.

"Alkylene" refers to divalent saturated aliphatic hydrocarbyl groups having from 1 to 25 carbon atoms and, in some embodiments, from 1 to 15 carbon atoms. The alkylene groups include branched and straight chain hydrocarbyl groups, such as methylene, ethylene, propylene, 2-methypropylene, pentylene, and the like.

"Heteroalkylene" refers to alkylene wherein 1-8 carbon atoms, are replaced with a heteroatom, preferably, with one or more of —N(COR')—, —S—, —S(O)—, —S(O$_2$)—, and —O—, where R' is $C_1$-$C_6$ alkyl.

"Alkoxy" refers to the group —O-alkyl, and includes, by way of example, methoxy, ethoxy, n-propoxy, isopropoxy, n-butoxy, t-butoxy, sec-butoxy, and n-pentoxy.

"Aryl" refers to an aromatic group of from 6 to 14 carbon atoms and no ring heteroatoms and having a single ring (e.g., phenyl) or multiple condensed (fused) rings (e.g., naphthyl or anthryl). For multiple ring systems, the term "Aryl" applies when the point of attachment is at an aromatic carbon atom (e.g., 5,6,7,8 tetrahydronaphthalene-2-yl is an aryl group as its point of attachment is at the 2-position of the aromatic phenyl ring).

"Heteroaryl" refers to an aromatic group of from 5 to 14 ring atoms and 1-3 ring heteroatoms and having a single ring (e.g., furyl) or multiple condensed (fused) rings (e.g., benzofuryl). For multiple ring systems, the term "heteroaryl" applies when the point of attachment is at an aromatic ring atom containing at least one heteroatom.

"Aryloxy" refers to the group —O-Aryl.

"Halo" refers to F, Cl, Br, and/or I.

"Heteroatom" refers to nitrogen, sulfur, phosphorous, an oxidized forms thereof, and/or oxygen.

"Pg" refers to a protecting group. Protecting group are well known functional groups that when bound to a functional group, render the resulting protected functional group inert to the reaction to be conducted on other portions of the compound and the corresponding reaction condition, and which can be reacted to regenerate the original functionality under deprotection conditions. The protecting group is selected to be compatible with the remainder of the molecule. An —O-Pg group protects a hydroxyl functionality during the synthesis described here. Examples of hydroxyl protecting groups include, for instance, ethers such as benzyl, p-methoxybenzyl, p-nitrobenzyl, allyl, and trityl; dialkylsilylethers, such as dimethylsilyl ether, and trialkylsilyl ethers such as trimethylsilyl ether, triethylsilyl ether, and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates such as methyl, ethyl, 2,2,2-trichloroethyl, allyl, and benzyl. Additional examples of hydroxy protecting groups are found in standard reference works such as Greene and Wuts, Protective Groups in Organic Synthesis., 2d Ed., 1991, John Wiley & Sons, and McOmie Protective Groups in Organic Chemistry, 1975, Plenum Press. Methods for protecting and deprotecting hydroxyl groups disclosed herein can be found in the art, and specifically in Greene and Wuts, supra, and the references cited therein.

"Leaving group" refers to a moiety that can be replaced by a nucleophile. Examples of leaving groups include but are not limited to halo and sulfonates.

As used herein, "polymers" provided herein do not include polymers created by substitution of a substitution. Should such substitution of substitution give rise to potential polymers, such substitution is limited to 3 such substitutions.

Referring to the compound of Formula (I), in one embodiment, each of $R^2$-$R^8$ independently is $C_1$-$C_4$ alkyl or is -L-$R^9$. In another embodiment, 1-7 of $R^2$-$R^8$ are -L-$R^9$. In another embodiment, 2-7 or 3-6 of $R^2$-$R^8$ are -L-$R^9$. In another embodiment, 1-6 of $R^2$-$R^8$ is $C_1$-$C_4$ alkyl. In another embodiment, 1-6 of $R^2$-$R^8$ is methyl. In another embodiment, at least one of $R^2$-$R^8$ is hydrogen.

In another embodiment, the polymerizable group is selected from the group consisting of —NCO, —NCS, —CO$_2$$R^{11}$, -ethynyl, —N$_3$, allyl or is

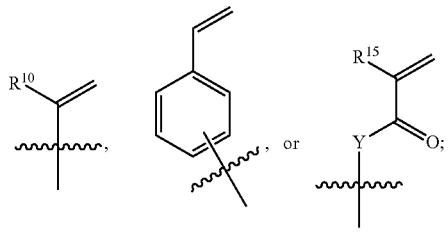

wherein $R^{10}$ is selected from the group consisting of hydrogen, $C_1$-$C_6$ alkyl, CO$_2$H, CO$_2$$R^{12}$, CN, and CON($R^{13}$)$_2$;

$R^{11}$ is a phenyl substituted with 4 or 5 fluoro atoms, or is succinimidyl or phthalimidyl;

$R^{12}$ is $C_1$-$C_{12}$ alkyl optionally substituted with 1-3 hydroxy groups;

$R^{13}$ $C_1$-$C_{12}$ alkyl optionally substituted with 1-3 hydroxy groups or the 2 $R^{13}$ groups together with the nitrogen atoms they are bound to form a 5-7 membered heterocyclic ring having 1 to 3 heteroatoms selected from oxygen, sulfur, nitrogen or NR$^{14}$ where $R^{14}$ is hydrogen or $C_1$-$C_{12}$ alkyl;

$R^{15}$ is selected from the group consisting of hydrogen, $C_1$-$C_6$ alkyl optionally substituted with 1-3 hydroxy groups, and CN;

Y is O or NR$^{16}$; and $R^{16}$ is hydrogen or $C_1$-$C_6$ alkyl.

In another embodiment, L is $C_1$-$C_{20}$ alkylene or heteroalkylene having 1 to 5 heteroatoms selected from oxygen, sulfur, and nitrogen, each of which is optionally substituted with 1-10 substituents selected from the group consisting of oxo (=O), thio (=S), and $C_1$-$C_6$ alkyl. Non-limiting examples of alkylene include —(CH$_2$)$_n$— where n is 1-12. In another embodiment, L is a covalent bond.

In another embodiment, the compound of Formula (I) is of Formula (I-B):

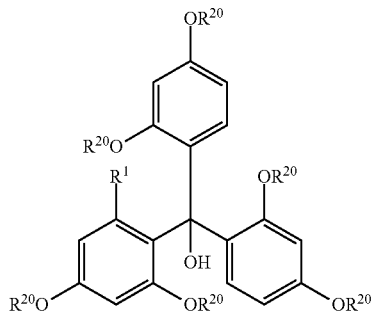

(I-C)

wherein
R$^1$ is hydrogen or —OR$^{20}$;
each R$^{20}$ independently is methyl, vinyl, allyl, —(CH$_2$)$_m$—OCOCH=CH$_2$, or —(CH$_2$)$_m$—OCOC(Me)=CH$_2$, provided that at least one R$^{20}$ is not methyl; and
m is 2-10.

In another embodiment, for the compound of Formula (I-B), 1, 2, or 3 R$^{20}$ groups are vinyl or allyl. In another embodiment, for the compound of Formula (I-B), 1, 2, or 3 R$^{20}$ groups are —(CH$_2$)$_m$—OCOC(Me)=CH$_2$. In another embodiment, for the compound of Formula (I-B), 1, 2, or 3 R$^{20}$ groups are —(CH$_2$)$_m$—OCOCH=CH$_2$. Such groups will result in the formation of an ethylene, propylene, or another higher alkylene group covalently attached at one end to the remainder of the indicator and at the other end to the polymeric chain. A polymerizable group, such as an acrylate or a methacrylate, is contemplated to polymerize the compounds of this invention with another monomer such as hydroxyethyl methacrylate. As these groups mimic the methyl group of the methoxy moiety of both hexamethoxy red and heptamethoxy red, their inclusion should minimally alters the pKa of the indicator. That is to say that the pKa should changed by no more than ±0.5, preferably by no more than ±0.3, and even preferably by no more than ±0.2 units.

The inclusion of one or more X substituents on the phenyl ring(s) allow for modulating the pKa of the indicator or for modulating the stability of the trisubstituted methyl cation formed when the hydroxy group is protonated and leaves as water, in a manner consistent with the pH desired for color transformation of the indicator. A nonlimiting process of water elimination and color generation is schematically depicted below:

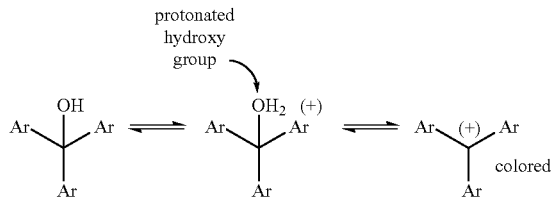

wherein each Ar independently refers to aryl moieties shown in the compounds provided herein, for example, of Formula (I) and (II). That is to say that introducing an electron donating and/or a cation stabilizing substituent such as, without limitation, alkoxy, alkyl, and aryl, provide an indicator, which changes color at lower acidity and higher pH. On the other hand, introducing an electron withdrawing substituent such, without limitation, halo or cyano, will provide for an indicator, which changes color at higher acidity and lower pH.

The compounds of this invention are synthesized following art recognized methods with the appropriate substitution of commercially available reagents as needed. Other compounds are synthesized following modifications of the methods illustrated herein, and those known, based on this disclosure. See, for example, Raj. B. Durairaj, Resorcinol: Chemistry, Technology, and Applications, Birkhäuser, 2005. Illustrative and non-limiting methods for synthesizing the compounds of this invention are schematically shown below which show the synthesis of an intermediate 4-hydroxyphenyl compound. Such intermediates are also within the scope of this invention. That compound is subsequently modified on the hydroxyl group to incorporate the polymerizable group.

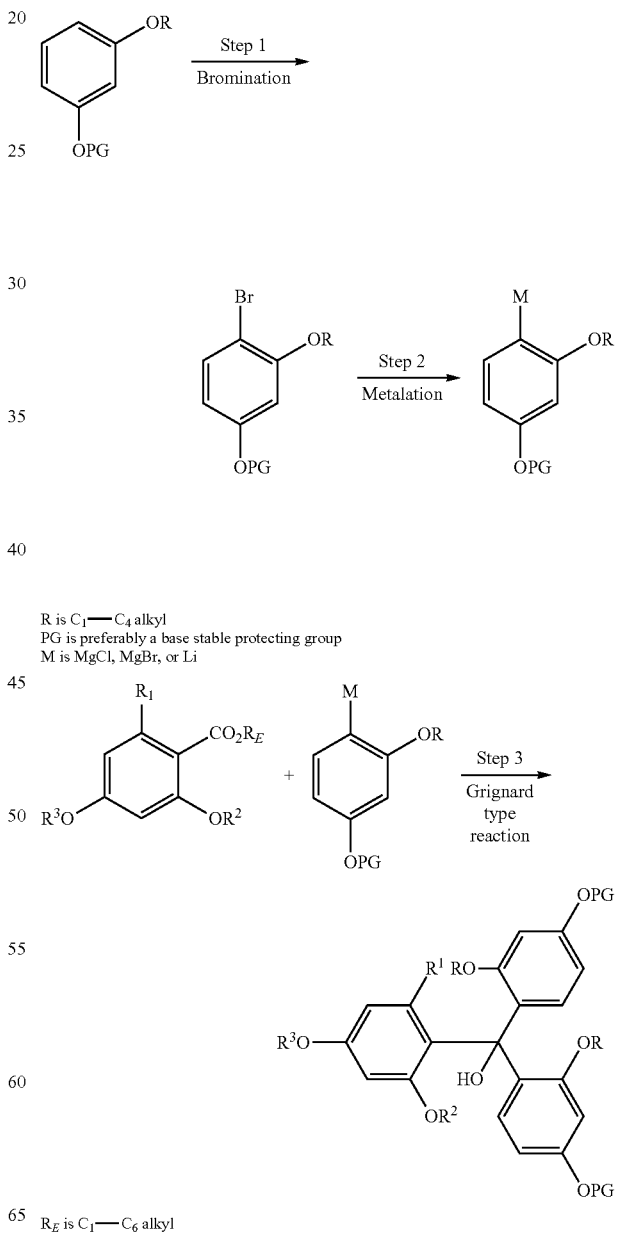

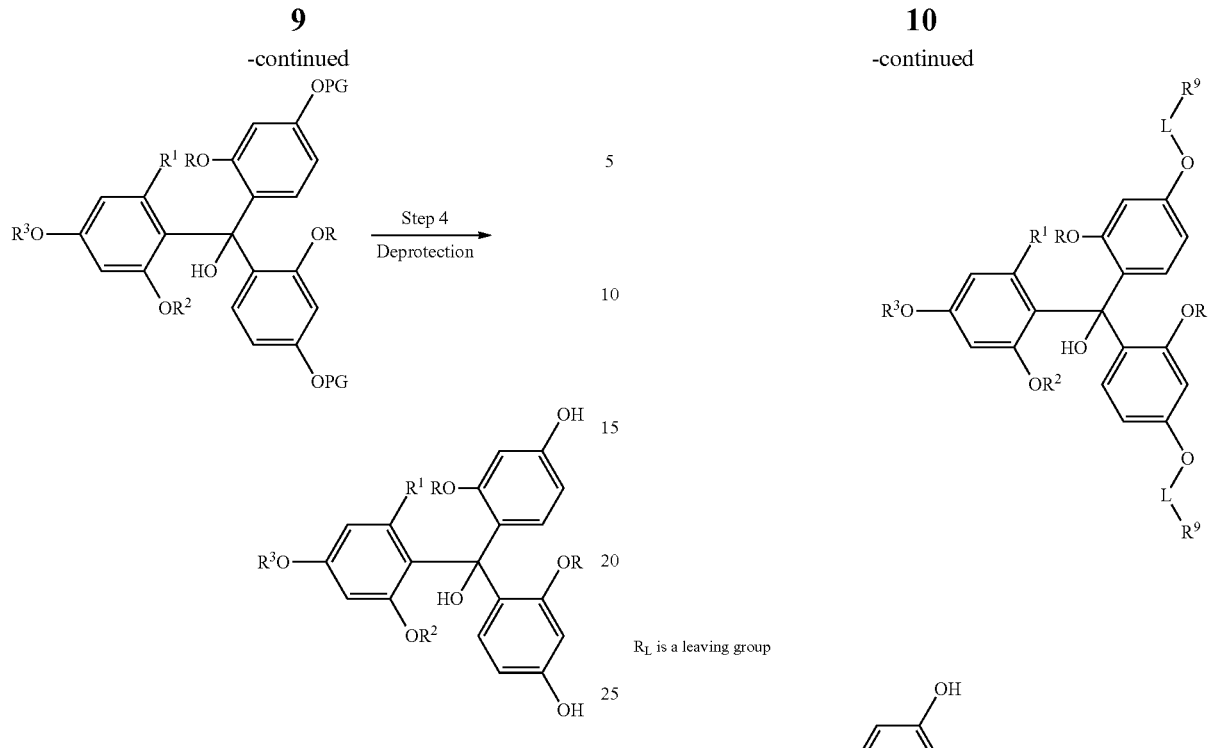

$R_L$ is a leaving group $L_1$ is a linker such as alkylene or heteroalkylene
$X^4$ is a protected OH, $NH_2$, or a $CO_2H$ group In step 1, a protected resorcinol methyl ether is brominated, preferably using 1 equivalent of bromine in a non-polar solvent such as dioxane. As used herein, PG refers to a protecting group, which refers to well known functional groups that, when bound to a functional group, render the resulting protected functional group inert to the reaction to be conducted on other portions of the compound and the corresponding reaction condition, and which can be reacted to regenerate the original functionality under deprotection conditions. Examples of protecting groups useful for synthesizing the compounds of this invention, and methods for protection and deprotection employed herein, are found in standard reference works such as Greene and Wuts, Protective Groups in Organic Synthesis., 2d Ed., 1991, John Wiley & Sons, and McOmie Protective Groups in Organic Chemistry, 1975, Plenum Press. Methylthiomethyl ether and allyl ethers are certain non-limiting protecting groups contemplated for the scheme above. In step 2, the brominated resorcinol derivative is metalated to provide a Grignard reagent or a resorcyl lithium. In step 3, the metalated aryl is reacted with an aryl carboxylic acid ester to provide a protected precursor to the compound of Formula (I), which is deprotected in step 4.

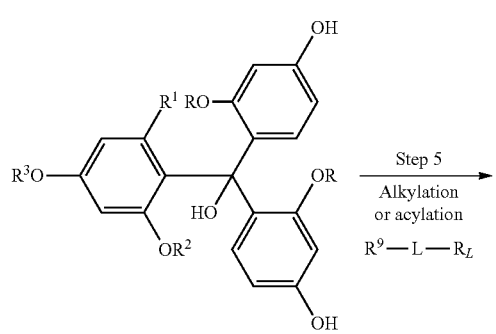

In step 5, the deprotected phenolic hydroxy compound is reacted with an $R^9$-L moiety containing a leaving group such as chloro, bromo, iodo, or $-OSO_2R_S$ where $R_S$ is $C_1$-$C_6$ alkyl optionally substituted with 1-5 fluoro atoms or aryl optionally substituted with 1-3 $C_1$-$C_6$ alkyl or halo groups. Alternatively, the deprotected compound is reacted with a compound that provides part of the linker L (step 6). Such compounds are elaborated to a compound of this invention as shown in steps 7 and 8 below using reagents and methods well known to the skilled artisan.

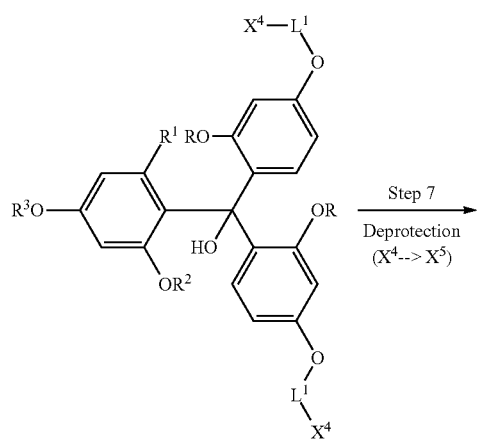
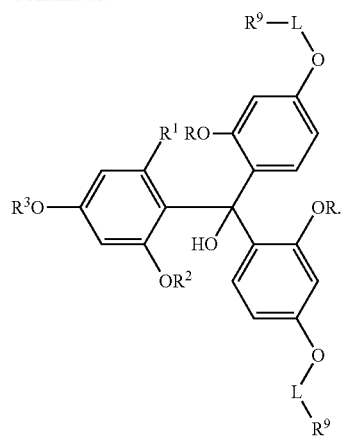
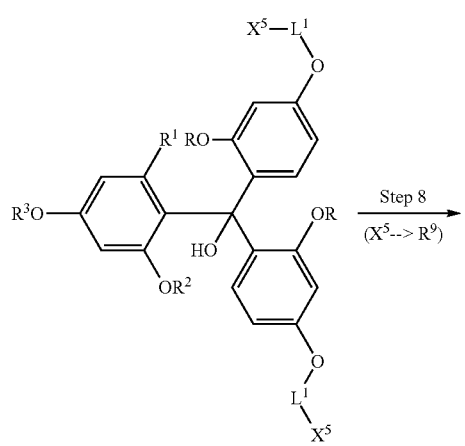
$X^5$ is OH, $NH_2$, or —$CO_2R_E$
The compounds of Formula (I) are also synthesized by reacting an appropriately protected aryl carboxylic acid ester with the metalated aryl compound and elaborating the triaryl methyl compounds produced, via methods provided herein and/or via methods well known to the skilled artisan:
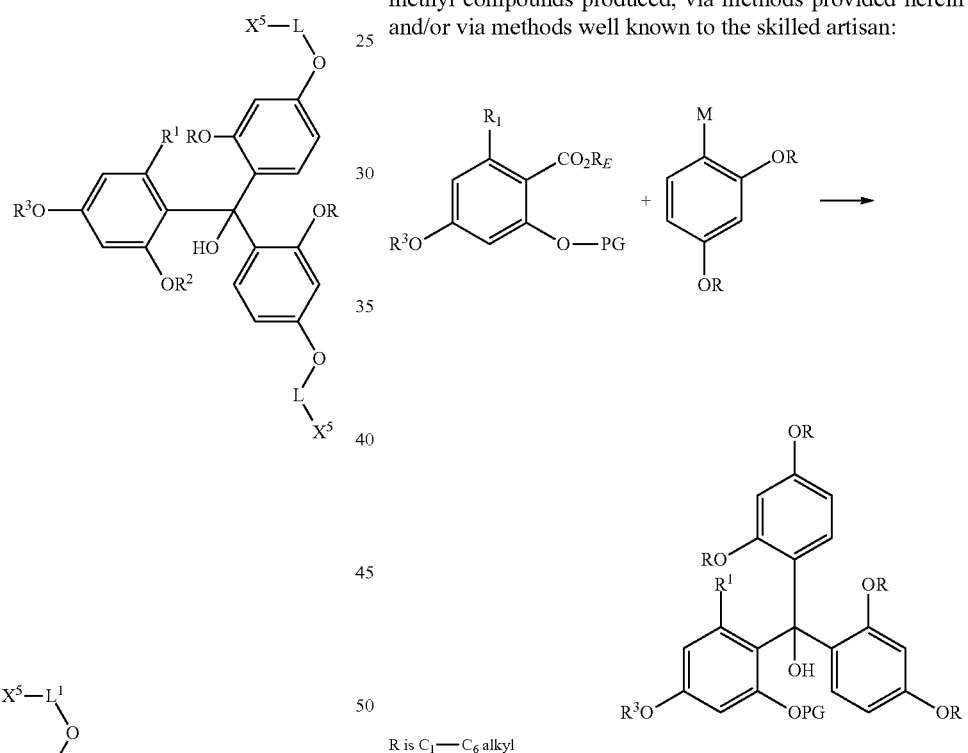
R is $C_1$—$C_6$ alkyl
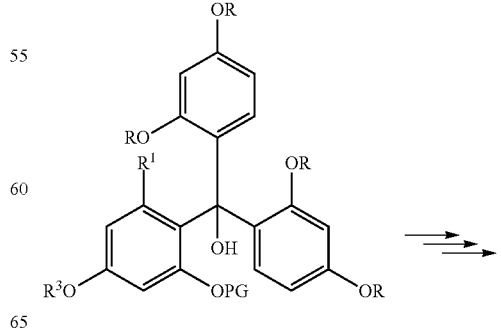

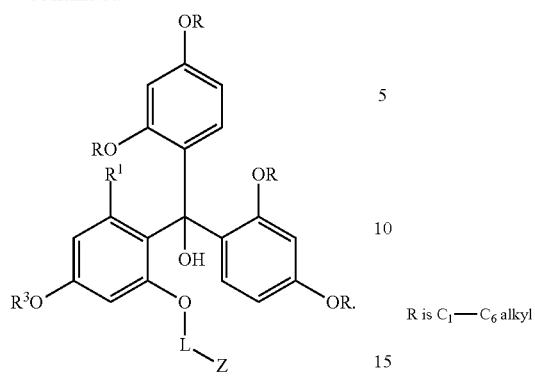

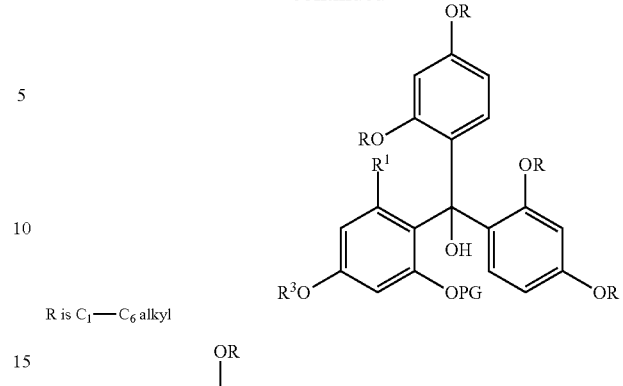

R is $C_1$—$C_6$ alkyl

The compounds of Formula (I) are also synthesized by reacting an appropriately protected aryl carboxylic acid ester with the metalated aryl compound and elaborating the triaryl methyl compounds produced, via methods provided herein and/or via methods well known to the skilled artisan:

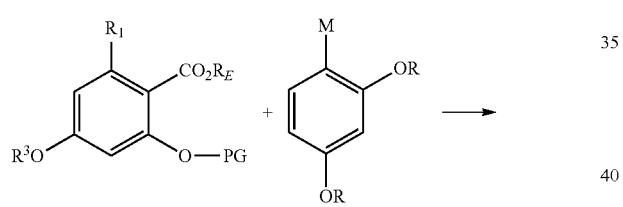

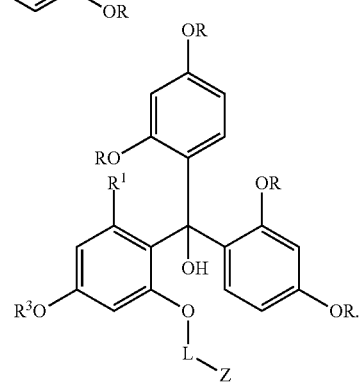

Compounds of Formula (I-B) are synthesized, for example, starting from commercially available hexamethoxy red or heptamethoxy red as shown below.

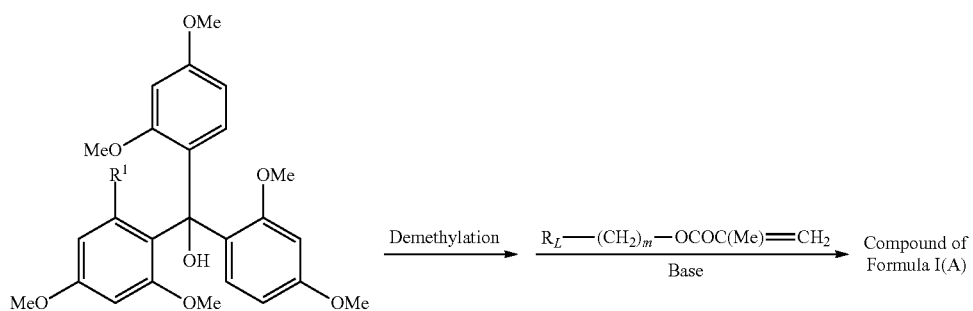

$R^1$ = H (hexamethoxy red)
$R^1$ = OMe (heptamethoxy red).

The demethylation can be performed following various methods well known in the art, such as, for example, reacting with an alkyl thiolate, such as isopropyl thiolate, ethyl thiolate, or diethylaminoethyl thiolate, or reacting with amides such as NaN(SiMe$_3$) and LiN(i-Pr)$_2$. See also Greene and Wuts supra. Various alkali metal carbonates are useful bases.

Other compounds of this invention are conveniently synthesized following these and other known methods upon appropriate substitution of starting material and, if needed, protecting groups. Electron withdrawing substituents such as halo can be conveniently incorporated into the aryl rings by electrophilic substitution employing hypohalite, halogens, ICl, preferably under alkaline conditions. A halo group is conveniently converted to a cyano group following well known methods, such as those employing CuCN. A nitro group is conveniently incorporated by electrophilic nitration employing various conditions and reagents well known to the skilled artisan, such as nitronium tetrafluoroborate, nitric acid, optionally with acetic anhydride, and the likes.

Other compounds of this invention, for example, those including one or more heteroaryl A, B, and C rings, are prepared following methods well known to the skilled artisan, or following methods illustrated here, upon appropriate substitution of starting material and reaction conditions as will be apparent to the skilled artisan upon reading this disclosure.

The reactions are carried out, preferably in an inert solvent, for a period of time sufficient to provide a substantial amount of the product, which is detected following well known methods such as thin layer chromatography or $^1$H-nuclear magnetic resonance spectrometry. The products are used for the subsequent steps without further purification or can be purified following well known methods such as one or more of column chromatography, crystallization, precipitation, and distillation under reduced pressure.

Other compounds of this invention are prepared following methods well known to a skilled artisan and/or those disclosed herein upon appropriate substitution of reactants and reagents.

It is contemplated that the pH sensitivity of the compounds of Formulas (I) and (II), wherein $R^1$ is hydrogen, is within ±0.5, preferably, within ±0.3, more preferably within ±0.2 of that of hexamethoxy red. It is also contemplated that pH sensitivity of the compounds of Formula (I), wherein $R^1$ is —OR$^8$, is within ±0.5, preferably, within ±0.3, more preferably within ±0.2 of that of heptamethoxy red. Compounds within the scope of this invention include but are not limited to those set forth in the Tables below.

Preferred Compounds of Formula (I-A)

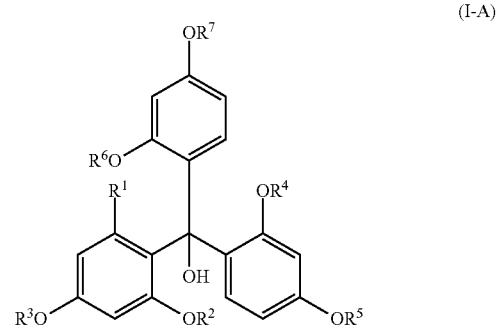

(I-A)

TABLE 1

| Ex. No. | R$_1$ | R$_2$, R$_4$, R$_6$ | R$_3$ | R$_5$ | R$_7$ |
|---|---|---|---|---|---|
| 1 | H | —CH$_3$ | —CH$_3$ | —CH$_3$ | —CH$_2$CH=CH$_2$ |
| 2 | H | —CH$_3$ | —CH$_2$CH=CH$_2$ | —CH$_3$ | —CH$_3$ |
| 3 | H | —CH$_3$ | —CH$_3$ | —CH$_2$CH=CH$_2$ | —CH$_3$ |
| 4 | H | —CH$_3$ | —CH$_2$CH=CH$_2$ | —CH$_2$CH=CH$_2$ | —CH$_3$ |
| 5 | H | —CH$_3$ | —CH$_3$ | —CH$_2$CH=CH$_2$ | —CH$_2$CH=CH$_2$ |
| 6 | H | —CH$_3$ | —CH$_2$CH=CH$_2$ | —CH$_3$ | —CH$_2$CH=CH$_2$ |
| 7 | H | —CH$_3$ | —CH$_2$CH=CH$_2$ | —CH$_2$CH=CH$_2$ | —CH$_2$CH=CH$_2$ |
| 8 | H | —CH$_3$ | —CH$_3$ | —CH$_3$ | —CH$_2$CH$_2$OC(O)CH=CH$_2$ 2-(acryl)ethylene |
| 9 | H | —CH$_3$ | —CH$_3$ | 2-(acryl)ethylene | —CH$_3$ |
| 10 | H | —CH$_3$ | 2-(acryl)ethylene | 2-(acryl)ethylene | —CH$_3$ |
| 11 | H | —CH$_3$ | Allyl | acrylate | —CH$_3$ |
| 12 | H | —CH$_3$ | —(CH$_2$)$_n$NCO where n = 2-12 | —(CH$_2$)$_n$NCS where n = 2-12 | —CH$_3$ |
| 13 | H | —CH$_3$ | —(CH$_2$)$_n$NCO where n = 2-12 | —(CH$_2$)$_n$NCO where n = 2-12 | —CH$_3$ |
| 14 | H | —CH$_3$ | —(CH$_2$)$_n$NCS where n = 2-12 | —(CH$_2$)$_n$NCS where n = 2-12 | —CH$_3$ |
| 15 | H | —CH$_3$ | —(CH$_2$)$_n$CO$_2$Ar$_F$ where Ar$_F$ is penta or tetrafluorophenyl | —(CH$_2$)$_n$CO$_2$Ar$_F$ where Ar$_F$ is penta or tetrafluorophenyl | —CH$_3$ |
| 16 | H | —CH$_3$ | —(CH$_2$)$_n$N$_3$ where n = 2-12 | —(CH$_2$)$_n$N$_3$ where n = 2-12 | —CH$_3$ |
| 17 | H | —CH$_3$ | —(CH$_2$)$_n$CCH where n = 2-12 | —(CH$_2$)$_n$CCH where n = 2-12 | —CH$_3$ |
| 18 | H | —CH$_3$ | —(CH$_2$)$_n$NCO where n = 2-12 | —(CH$_2$)$_n$NCO where n = 2-12 | —CH$_3$ |
| 19 | H | —CH$_3$ | —CH$_3$ | —(CH$_2$)$_n$NCS where n = 2-12 | —CH$_3$ |
| 20 | H | —CH$_3$ | —CH$_3$ | —(CH$_2$)$_n$CO$_2$Ar$_F$ where ArF is penta or tetrafluorophenyl | —CH$_3$ |
| 21 | H | —CH$_3$ | —CH$_3$ | —(CH$_2$)$_n$N$_3$ where n = 2-12 | —CH$_3$ |
| 22 | H | —CH$_3$ | —CH$_3$ | —(CH$_2$)$_n$CCH where n = 2-12 | —CH$_3$ |

TABLE 1-continued

| Ex. No. | $R_1$ | $R_2, R_4, R_6$ | $R_3$ | $R_5$ | $R_7$ |
|---|---|---|---|---|---|
| 23 | —OMe | —CH$_3$ | —CH$_3$ | —CH$_3$ | —CH$_2$CH=CH$_2$ |
| 24 | —OMe | —CH$_3$ | —CH$_2$CH=CH$_2$ | —CH$_3$ | —CH$_3$ |
| 25 | —OMe | —CH$_3$ | —CH$_3$ | —CH$_2$CH=CH$_2$ | —CH$_3$ |
| 26 | —OMe | —CH$_3$ | —CH$_2$CH=CH$_2$ | —CH$_2$CH=CH$_2$ | —CH$_3$ |
| 27 | —OMe | —CH$_3$ | —CH$_3$ | —CH$_2$CH=CH$_2$ | —CH$_2$CH=CH$_2$ |
| 28 | —OMe | —CH$_3$ | —CH$_2$CH=CH$_2$ | —CH$_3$ | —CH$_2$CH=CH$_2$ |
| 29 | —OMe | —CH$_3$ | —CH$_2$CH=CH$_2$ | —CH$_2$CH=CH$_2$ | —CH$_2$CH=CH$_2$ |
| 30 | —OMe | —CH$_3$ | —CH$_3$ | —CH$_3$ | —CH$_2$CH$_2$OC(O)CH=CH$_2$ 2-(acryl)ethylene |
| 31 | —OMe | —CH$_3$ | —CH$_3$ | 2-(acryl)ethylene | —CH$_3$ |
| 32 | —OMe | —CH$_3$ | 2-(acryl)ethylene | 2-(acryl)ethylene | —CH$_3$ |
| 33 | —OMe | —CH$_3$ | Allyl | acrylate | —CH$_3$ |
| 34 | —OMe | —CH$_3$ | —(CH$_2$)$_n$NCO where n = 2-12 | —(CH$_2$)$_n$NCS where n = 2-12 | —CH$_3$ |
| 35 | —OMe | —CH$_3$ | —(CH$_2$)$_n$NCO where n = 2-12 | —(CH$_2$)$_n$NCO where n = 2-12 | —CH$_3$ |
| 36 | —OMe | —CH$_3$ | —(CH$_2$)$_n$NCS where n = 2-12 | —(CH$_2$)$_n$NCS where n = 2-12 | —CH$_3$ |
| 37 | —OMe | —CH$_3$ | —(CH$_2$)$_n$CO$_2$Ar$_F$ where Ar$_F$ is penta or tetrafluorophenyl | —(CH$_2$)$_n$CO$_2$Ar$_F$ where Ar$_F$ is penta or tetrafluorophenyl | —CH$_3$ |
| 38 | —OMe | —CH$_3$ | —(CH$_2$)$_n$N$_3$ where n = 2-12 | —(CH$_2$)$_n$N$_3$ where n = 2-12 | —CH$_3$ |
| 39 | —OMe | —CH$_3$ | —(CH$_2$)$_n$CCH where n = 2-12 | —(CH$_2$)$_n$CCH where n = 2-12 | —CH$_3$ |
| 40 | —OMe | —CH$_3$ | —(CH$_2$)$_n$NCO where n = 2-12 | —(CH$_2$)$_n$NCO where n = 2-12 | —CH$_3$ |
| 41 | —OMe | —CH$_3$ | —CH$_3$ | —(CH$_2$)$_n$NCS where n = 2-12 | —CH$_3$ |
| 42 | —OMe | —CH$_3$ | —CH$_3$ | —(CH$_2$)$_n$CO$_2$Ar$_F$ where Ar$_F$ is penta or tetrafluorophenyl | —CH$_3$ |
| 43 | —OMe | —CH$_3$ | —CH$_3$ | —(CH$_2$)$_n$N$_3$ where n = 2-12 | —CH$_3$ |
| 44 | —OMe | —CH$_3$ | —CH$_3$ | —(CH$_2$)$_n$CCH where n = 2-12 | —CH$_3$ |
| 45 | H | —CH$_3$ | —(CH$_2$)$_n$OC(O)-CH=CH$_2$ where n = 2-12 | —(CH$_2$)$_n$OC(O)-CH=CH$_2$ where n = 2-12 | —CH$_3$ |
| 46 | H | —CH$_3$ | —CH$_3$ | —(CH$_2$)$_n$OC(O)-CH=CH$_2$ where | —CH$_3$ |
| 47 | —OMe | —CH$_3$ | —(CH$_2$)$_n$OC(O)-CH=CH$_2$ where n = 2-12 | —(CH$_2$)$_n$OC(O)-CH=CH$_2$ where n = 2-12 | —CH$_3$ |
| 48 | —OMe | —CH$_3$ | —CH$_3$ | —(CH$_2$)$_n$OC(O)-CH=CH$_2$ where n = 2-12 | —CH$_3$ |

Preferred compounds of Formula (I-B):

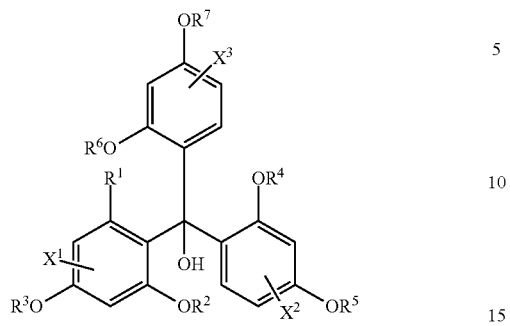

TABLE 2

| Ex. No. | $R^1$ | $R^2$, $R^4$, $R^6$ | $R^3$ | $R^5$ | $R^7$ | $X^1$ | $X^2$ | $X^3$ |
|---|---|---|---|---|---|---|---|---|
| 1 | H | —CH$_3$ | —CH$_3$ | —CH$_3$ | —CH$_2$CH=CH$_2$ | H/—OMe/Me/Ar$^1$ | H/—OMe/Me/Ar$^1$ (refers to phenyl and 4-methoxyphenyl) | OMe/Me/Ar$^1$ |
| 2 | H | —CH$_3$ | —CH$_2$CH=CH$_2$ | —CH$_3$ | —CH$_3$ | H/—OMe/Me/Ar$^1$ | H/—OMe/Me/Ar$^1$ | OMe/Me/Ar$^1$ |
| 3 | H | —CH$_3$ | —CH$_3$ | —CH$_2$CH=CH$_2$ | —CH$_3$ | H/—OMe/Me/Ar$^1$ | H/—OMe/Me/Ar$^1$ | OMe/Me |
| 4 | H | —CH$_3$ | —CH$_2$CH=CH$_2$ | —CH$_2$CH=CH$_2$ | —CH$_3$ | H/—OMe/Me/Ar$^1$ | H/—OMe/Me/Ar$^1$ | /Ar$^1$ |
| 5 | H | —CH$_3$ | —CH$_3$ | —CH$_2$CH=CH$_2$ | —CH$_2$CH=CH$_2$ | H/—OMe/Me/Ar$^1$ | H/—OMe/Me/Ar$^1$ | OMe/Me |
| 6 | H | —CH$_3$ | —CH$_2$CH=CH$_2$ | —CH$_3$ | —CH$_2$CH=CH$_2$ | H/—OMe/Me/Ar$^1$ | H/—OMe/Me/Ar$^1$ | /Ar$^1$ |
| 7 | H | —CH$_3$ | —CH$_2$CH=CH$_2$ | —CH$_2$CH=CH$_2$ | —CH$_2$CH=CH$_2$ | H/—OMe/Me/Ar$^1$ | H/—OMe/Me/Ar$^1$ | OMe/Me |
| 8 | H | —CH$_3$ | —CH$_3$ | —CH$_3$ | —CH$_2$CH$_2$O—C(O)CH=CH$_2$ (2-(acryl)ethylene) | H/—OMe/Me/Ar$^1$ | H/—OMe/Me/Ar$^1$ | /Ar$^1$ |
| 9 | H | —CH$_3$ | —CH$_3$ | 2-(acryl)ethylene | —CH$_3$ | H/—OMe/Me/Ar$^1$ | H/—OMe/Me/Ar$^1$ | OMe/Me |
| 10 | H | —CH$_3$ | 2-(acryl)ethylene | 2-(acryl)ethylene | —CH$_3$ | H/—OMe/Me/Ar$^1$ | H/—OMe/Me/Ar$^1$ | /Ar$^1$ |
| 11 | H | —CH$_3$ | Allyl | acrylate | —CH$_3$ | H/—OMe/Me/Ar$^1$ | H/—OMe/Me/Ar$^1$ | OMe/Me |
| 12 | H | —CH$_3$ | —(CH$_2$)$_n$NCO where n = 2-12 | —(CH$_2$)$_n$NCS where n = 2-12 | —CH$_3$ | H/—OMe/Me/Ar$^1$ | H/—OMe/Me/Ar$^1$ | /Ar$^1$ |
| 13 | H | —CH$_3$ | —(CH$_2$)$_n$NCO where n = 2-12 | —(CH$_2$)$_n$NCO where n = 2-12 | —CH$_3$ | H/—OMe/Me/Ar$^1$ | H/—OMe/Me/Ar$^1$ | OMe/Me |
| 14 | H | —CH$_3$ | —(CH$_2$)$_n$NCS where n = 2-12 | —(CH$_2$)$_n$NCS where n = 2-12 | —CH$_3$ | H/—OMe/Me/Ar$^1$ | H/—OMe/Me/Ar$^1$ | /Ar$^1$ |
| 15 | H | —CH$_3$ | —(CH$_2$)$_n$CO$_2$Ar$_F$ where Ar$_F$ is penta or tetrafluorophenyl | —(CH$_2$)$_n$CO$_2$Ar$_F$ where Ar$_F$ is penta or tetrafluorophenyl | —CH$_3$ | H/—OMe/Me/Ar$^1$ | H/—OMe/Me/Ar$^1$ | OMe/Me |
| 16 | H | —CH$_3$ | —(CH$_2$)$_n$N$_3$ where n = 2-12 | —(CH$_2$)$_n$N$_3$ where n = 2-12 | —CH$_3$ | H/—OMe/Me/Ar$^1$ | H/—OMe/Me/Ar$^1$ | /Ar$^1$ |
| 17 | H | —CH$_3$ | —(CH$_2$)$_n$CCH where n = 2-12 | —(CH$_2$)$_n$CCH where n = 2-12 | —CH$_3$ | H/—OMe/Me/Ar$^1$ | H/—OMe/Me/Ar$^1$ | OMe/Me |
| 18 | H | —CH$_3$ | —(CH$_2$)$_n$NCO where n = 2-12 | —(CH$_2$)$_n$NCO where n = 2-12 | —CH$_3$ | H/—OMe/Me/Ar$^1$ | H/—OMe/Me/Ar$^1$ | /Ar$^1$ |
| 19 | H | —CH$_3$ | —CH$_3$ | —(CH$_2$)$_n$NCS where n = 2-12 | —CH$_3$ | H/—OMe/Me/Ar$^1$ | H/—OMe/Me/Ar$^1$ | OMe/Me |
| 20 | H | —CH$_3$ | —CH$_3$ | —(CH$_2$)$_n$CO$_2$Ar$_F$ where Ar$_F$ is penta or tetrafluorophenyl | —CH$_3$ | H/—OMe/Me/Ar$^1$ | H/—OMe/Me/Ar$^1$ | /Ar$^1$ |
| 21 | H | —CH$_3$ | —CH$_3$ | —(CH$_2$)$_n$N$_3$ where n = 2-12 | —CH$_3$ | H/—OMe/Me/Ar$^1$ | H/—OMe/Me/Ar$^1$ | OMe/Me |
| 22 | H | —CH$_3$ | —CH$_3$ | —(CH$_2$)$_n$CCH where n = 2-12 | —CH$_3$ | H/—OMe/Me/Ar$^1$ | H/—OMe/Me/Ar$^1$ | /Ar$^1$ |

TABLE 2-continued

| Ex. No. | $R^1$ | $R^2$, $R^4$, $R^6$ | $R^3$ | $R^5$ | $R^7$ | $X^1$ | $X^2$ | $X^3$ |
|---|---|---|---|---|---|---|---|---|
| 23 | —OMe | —CH$_3$ | —CH$_3$ | —CH$_3$ | —CH$_2$CH=CH$_2$ | H/—OMe/ Me/Ar$^1$ | H/—OMe/ Me/Ar$^1$ | OMe/ Me |
| 24 | —OMe | —CH$_3$ | —CH$_2$CH=CH$_2$ | —CH$_3$ | —CH$_3$ | H/—OMe/ Me/Ar$^1$ | H/—OMe/ Me/Ar$^1$ | /Ar$^1$ |
| 25 | —OMe | —CH$_3$ | —CH$_3$ | —CH$_2$CH=CH$_2$ | —CH$_3$ | H/—OMe/ Me/Ar$^1$ | H/—OMe/ Me/Ar$^1$ | OMe/ Me |
| 26 | —OMe | —CH$_3$ | —CH$_2$CH=CH$_2$ | —CH$_2$CH=CH$_2$ | —CH$_3$ | H/—OMe/ Me/Ar$^1$ | H/—OMe/ Me/Ar$^1$ | /Ar$^1$ |
| 27 | —OMe | —CH$_3$ | —CH$_3$ | —CH$_2$CH=CH$_2$ | —CH$_2$CH=CH$_2$ | H/—OMe/ Me/Ar$^1$ | H/—OMe/ Me/Ar$^1$ | OMe/ Me |
| 28 | —OMe | —CH$_3$ | —CH$_2$CH=CH$_2$ | —CH$_3$ | —CH$_2$CH=CH$_2$ | H/—OMe/ Me/Ar$^1$ | H/—OMe/ Me/Ar$^1$ | /Ar$^1$ |
| 29 | —OMe | —CH$_3$ | —CH$_2$CH=CH$_2$ | —CH$_2$CH=CH$_2$ | —CH$_2$CH=CH$_2$ | H/—OMe/ Me/Ar$^1$ | H/—OMe/ Me/Ar$^1$ | OMe/ Me |
| 30 | —OMe | —CH$_3$ | —CH$_3$ | —CH$_3$ | —CH$_2$CH$_2$OC(O)CH=CH$_2$ 2-(acryl)ethylene) | H/—OMe/ Me/Ar$^1$ | H/—OMe/ Me/Ar$^1$ | /Ar$^1$ |
| 31 | —OMe | —CH$_3$ | —CH$_3$ | 2-(acryl)ethylene | —CH$_3$ | H/—OMe/ Me/Ar$^1$ | H/—OMe/ Me/Ar$^1$ | OMe/ Me |
| 32 | —OMe | —CH$_3$ | 2-(acryl)ethylene | 2-(acryl)ethylene | —CH$_3$ | H/—OMe/ Me/Ar$^1$ | H/—OMe/ Me/Ar$^1$ | /Ar$^1$ |
| 33 | —OMe | —CH$_3$ | Allyl | acrylate | —CH$_3$ | H/—OMe/ Me/Ar$^1$ | H/—OMe/ Me/Ar$^1$ | OMe/ Me |
| 34 | —OMe | —CH$_3$ | —(CH$_2$)$_n$NCO where n = 2-12 | —(CH$_2$)$_n$NCS where n = 2-12 | —CH$_3$ | H/—OMe/ Me/Ar$^1$ | H/—OMe/ Me/Ar$^1$ | /Ar$^1$ |
| 35 | —OMe | —CH$_3$ | —(CH$_2$)$_n$NCO where n = 2-12 | —(CH$_2$)$_n$NCO where n = 2-12 | —CH$_3$ | H/—OMe/ Me/Ar$^1$ | H/—OMe/ Me/Ar$^1$ | OMe/ Me |
| 36 | —OMe | —CH$_3$ | —(CH$_2$)$_n$NCS where n = 2-12 | —(CH$_2$)$_n$NCS where n = 2-12 | —CH$_3$ | H/—OMe/ Me/Ar$^1$ | H/—OMe/ Me/Ar$^1$ | /Ar$^1$ |
| 37 | —OMe | —CH$_3$ | —(CH$_2$)$_n$CO$_2$Ar$_F$ where Ar$_F$ is penta or tetrafluorophenyl | —(CH$_2$)$_n$CO$_2$Ar$_F$ where Ar$_F$ is penta or tetrafluorophenyl | —CH$_3$ | H/—OMe/ Me/Ar$^1$ | H/—OMe/ Me/Ar$^1$ | OMe/ Me |
| 38 | —OMe | —CH$_3$ | —(CH$_2$)$_n$N$_3$ where n = 2-12 | —(CH$_2$)$_n$N$_3$ where n = 2-12 | —CH$_3$ | H/—OMe/ Me/Ar$^1$ | H/—OMe/ Me/Ar$^1$ | /Ar$^1$ |
| 39 | —OMe | —CH$_3$ | —(CH$_2$)$_n$CCH where n = 2-12 | —(CH$_2$)$_n$CCH where n = 2-12 | —CH$_3$ | H/—OMe/ Me/Ar$^1$ | H/—OMe/ Me/Ar$^1$ | OMe/ Me |
| 40 | —OMe | —CH$_3$ | —(CH$_2$)$_n$NCO where n = 2-12 | —(CH$_2$)$_n$NCO where n = 2-12 | —CH$_3$ | H/—OMe/ Me/Ar$^1$ | H/—OMe/ Me/Ar$^1$ | /Ar$^1$ |
| 41 | —OMe | —CH$_3$ | —CH$_3$ | —(CH$_2$)$_n$NCS where n = 2-12 | —CH$_3$ | H/—OMe/ Me/Ar$^1$ | H/—OMe/ Me/Ar$^1$ | OMe/ Me |
| 42 | —OMe | —CH$_3$ | —CH$_3$ | —(CH$_2$)$_n$CO$_2$Ar$_F$ where Ar$_F$ is penta or tetrafluorophenyl | —CH$_3$ | H/—OMe/ Me/Ar$^1$ | H/—OMe/ Me/Ar$^1$ | /Ar$^1$ |
| 43 | —OMe | —CH$_3$ | —CH$_3$ | —(CH$_2$)$_n$N$_3$ where n = 2-12 | —CH$_3$ | H/—OMe/ Me/Ar$^1$ | H/—OMe/ Me/Ar$^1$ | OMe/ Me |
| 44 | —OMe | —CH$_3$ | —CH$_3$ | —(CH$_2$)$_n$CCH where n = 2-12 | —CH$_3$ | H/—OMe/ Me/Ar$^1$ | H/—OMe/ Me/Ar$^1$ | /Ar$^1$ |
| 45 | H | —CH$_3$ | —(CH$_2$)$_n$OC(O)CH=CH$_2$ where n = 2-12 | —(CH$_2$)$_n$OC(O)CH=CH$_2$ where n = 2-12 | —CH$_3$ | H/—OMe/ Me/Ar$^1$ | H/—OMe/ Me/Ar$^1$ | OMe/ Me |
| 46 | H | —CH$_3$ | —CH$_3$ | —(CH$_2$)$_n$OC(O)CH=CH$_2$ where n = 2-12 | —CH$_3$ | H/—OMe/ Me/Ar$^1$ | H/—OMe/ Me/Ar$^1$ | /Ar$^1$ |
| 47 | —OMe | —CH$_3$ | —(CH$_2$)$_n$OC(O)—CH=CH$_2$ where n = 2-12 | —(CH$_2$)$_n$OC(O)—CH=CH$_2$ where n = 2-12 | —CH$_3$ | H/—OMe/ Me/Ar$^1$ | H/—OMe/ Me/Ar$^1$ | OMe/ Me |
| 48 | —OMe | —CH$_3$ | —CH$_3$ | —(CH$_2$)$_n$OC(O)—CH=CH$_2$ where n = 2-12 | —CH$_3$ | H/—OMe/ Me/Ar$^1$ | H/—OMe/ Me/Ar$^1$ | /Ar$^1$ |

Preferred compounds of Formula (II-A)

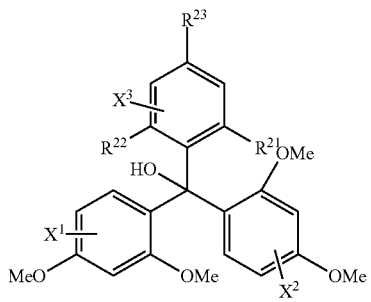

TABLE 3

| Ex. No. | $X^1$ | $X^2$ | $X^3$ | $R^{21}$ | $R^{22}$ | $R^{23}$ |
|---|---|---|---|---|---|---|
| | H | H | OMe | OMe | OMe | OMe |
| | H | OMe | OMe | OMe | OMe | OMe |
| | H | OMe | OMe | OMe | OMe | H |
| | H | OMe | OMe | OMe | H | OMe |
| | OMe | OMe | OMe | OMe | OMe | OMe |
| | H | H | Me | OMe | OMe | OMe |
| | H | Me | Me | OMe | OMe | OMe |
| | H | Me | Me | OMe | OMe | H |
| | H | Me | Me | OMe | H | OMe |
| | Me | Me | OMe | OMe | OMe | OMe |
| | Me | Me | Me | OMe | OMe | OMe |
| | H | H | Me | OMe | OMe | OMe |
| | H | $Ar^1$ (refers to phenyl and 4-methoxyphenyl) | $Ar^1$ | OMe | OMe | OMe |
| | H | $Ar^1$ | $Ar^1$ | OMe | OMe | H |
| | H | $Ar^1$ | $Ar^1$ | OMe | H | OMe |
| | $Ar^1$ | $Ar^1$ | OMe | OMe | OMe | OMe |
| | $Ar^1$ | $Ar^1$ | $Ar^1$ | OMe | OMe | OMe |

Certain preferred compounds of Formula (A)

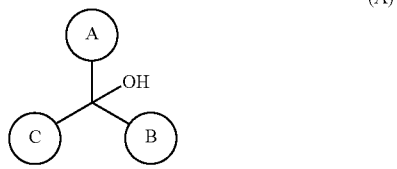

(A)

TABLE 4

| Ex. No. | A | B | C |
|---|---|---|---|
| | furyl optionally substituted with 1 or 2 methoxy groups | furyl optionally substituted with 1 or 2 methoxy groups | furyl optionally substituted with 1 or 2 methoxy groups |
| | furyl optionally substituted with 1 or 2 methoxy groups | furyl optionally substituted with 1 or 2 methoxy groups | 2,6-dimethoxyphenyl |
| | furyl optionally substituted with 1 or 2 methoxy groups | 2,6-dimethoxyphenyl | 2,6-dimethoxyphenyl |
| | thiophenyl optionally substituted with 1 or 2 methoxy groups | thiophenyl optionally substituted with 1 or 2 methoxy groups | thiophenyl optionally substituted with 1 or 2 methoxy groups |
| | thiophenyl optionally substituted with 1 or 2 methoxy groups | thiophenyl optionally substituted with 1 or 2 methoxy groups | 2,6-dimethoxyphenyl |
| | thiophenyl optionally substituted with 1 or 2 methoxy groups | 2,6-dimethoxyphenyl | 2,6-dimethoxyphenyl |

EXAMPLES

Example 1

Preparation of Heptamethoxy Red in Gram Scale

Step 1: Synthesis of Methyl 2,4,6-Trimethoxybenzoate 2,4,6-trimethoxybenzoic acid (5.61 g, 26.42 mmol) was suspended in 20 mL of methanol. Concentrated sulfuric acid (1 mL) was added to the mixture, and the reaction heated to reflux for 24 hrs. The reaction was cooled to room temperature, and the methanol removed in vacuo. The residues were taken up in 50 mL 5% $NaHCO_3$ and extracted with hexane until all the solids had dissolved. The hexane extract was dried over anhydrous $Na_2SO_4$, filtered, and the volatiles were removed in a rotary evaporator to dryness to give the desired product, methyl 2,4,6-trimethoxybenzoate, as a white crystalline solid.

Step 2: Synthesis of Heptamethoxy Red 1-bromo-2,4-dimethoxybenzene (4.23 g, 19.47 mmol) was added to a round bottom flask, and the flask flushed with nitrogen for 10 minutes. Anhydrous ether (80 mL) was added, followed by the drop wise addition of n-butyllithium in hexane (1.6M, 12.2 mL). The cloudy mixture was stirred at room temperature for 10 minutes. Methyl 2,4,6-trimethoxybenzoate (2.20 g, 9.74 mmol) was dissolved in ether, and added drop wise to the reaction mixture. After the addition was complete, the reaction was stirred for 3 minutes longer. The reaction was then poured into a separatory funnel containing 5% $NH_4Cl$ (50 mL) and shaken until a color change was observed. The layers were separated, and the ether layer was dried over anhydrous $Na_2SO_4$, filtered, and the volatiles were removed in a rotary evaporator to dryness. The crude oil was placed in the freezer. (Crude yield 6.02 g, 132%).

Example 2

One Step Preparation of Heptamethoxy Red

Add (4.23 g, 19.47 mmol) 1-bromo-2,4-dimethoxybenzene to an appropriately sized round bottom flask. Attach a rubber septum to seal the flask. Insert a needle into the septum as a vent and flush the round bottom flask with nitrogen for about 10 minutes. Add (80 mL) anhydrous ether, followed by the drop wise addition of n-butyllithium in hexane (1.6M, 12.2 mL). Stir the cloudy mixture for 10 minutes and keep the round bottom flask on ice. Dissolve (2.20 g, 9.74 mmol) of methyl 2,4,6-trimethoxybenzoate in about 20 ml of anhydrous ether (more than ~20 mL can be used if needed), and then add this drop wise to the reaction mixture. After the addition is complete, stir the reaction mixture for about 3 minutes longer. Pour the reaction mixture into a separatory funnel containing 5% NH₄Cl (aq) (50 mL) and shake until a color change is observed (pale orange). The layers are allowed to separated, and dry the top ether layer with about 5 g anhydrous Na₂SO₄, filter, and the volatiles were removed in a rotary evaporator to dryness at 35-40° C. under 400 mbar. Place the crude oil of heptamethoxy red (yellow-orange in color) into the freezer. Yield is ~3.1 g.

Example 3

Preparation of Hexamethoxy Red in Gram Scale

Add (4.23 g, 19.47 mmol) 1-bromo-2,4-dimethoxybenzene to an appropriately sized round bottom flask. Attach a rubber septum to seal the flask. Insert a needle into the septum as a vent and flush the round bottom flask with nitrogen for about 10 minutes. Add anhydrous ether (80 mL), followed by the drop wise addition of n-butyllithium in hexane (1.6M, 12.2 mL). Stir the cloudy mixture for 10 minutes and keep the round bottom flask on ice. Dissolve (2.20 g, 9.74 mmol) of methyl 2,4-dimethoxybenzoate in about 20 ml of anhydrous ether (if needed, more than about 20 ml can be used), and then add this drop wise to the reaction mixture. After the addition is complete, stir the reaction mixture for about 3 minutes longer. Pour the reaction mixture into a separatory funnel containing 5% NH₄Cl (aq) (50 mL) and shake until a color change is observed (pale orange). The layers are allowed to separated, and dry the top ether layer with about 5 g anhydrous Na₂SO₄, filter, and the volatiles were removed in a rotary evaporator to dryness at 35-40° C. under 400 mbar. Place the crude oil of hexamethoxy red (yellow-orange in color) into the freezer. Yield is about 3.1 g.

Example 4

Preparation of a Polymerizable Indicator of this Invention

Heptamethoxy red (1 molar equivalent) is heated with an alkyl thiol (1.2-5 molar equivalents) and sodium tertiary butoxide (1.2-5 molar equivalents) in DMF (about 0.5-2 moles/liter with respect to hexamethoxy red). The reaction is monitored for disappearance of hexamethoxy red and/or formation of hydroxylated compounds. When the reaction is substantially complete, the reaction mixture is cooled, Br—(CH₂)ₘ—OC(O)CH=CH₂, where m is 2-10 (preferably in the same molar equivalent as the thiolate), added in situ, and the reaction mixture heated again, if necessary. The polymerizable indicator is isolated from the reaction mixture following aqueous work up and separated by chromatography preferably under neutral to slightly basic conditions, such as by employing neutral or basic alumina, or by employing a slightly alkaline eluent such as an eluent spiked with triethyl amine.

UTILITY

The compounds of this invention are useful as pH indicators, particularly when polymerized, such as with another monomer such as hydroxyethyl methacrylate. The pH indicators of this invention and the polymers including the monomers of this invention are useful in contact lenses, food packaging, and bandages.

The polymerizable group is chosen relative to the polymer to be formed. For example, allyl and 2-(acryl)ethylene are readily incorporated into polyacrylates, polymethacrylates, polymers of HEMA (2-hydroxylethylene methacrylate), polyvinylacetate, polyvinylalcohol, polystyrene, and the like. Because the pH indicators of this invention have been functionalized to include reactive functionality similar to the monomer to be polymerized, one can form either random copolymers of the monomer and the pH indicator or block copolymers where the pH indicator is limited to a very specific part of the polymer. The latter allows only a portion of the polymer to provide pH indication.

Similarly, isocyanate and thioisocyanates are readily incorporated into peptides and proteins through appropriate functional groups such as amino or hydroxyl functionalities as well as through carbohydrates via one or more of their hydroxyl functionalities. In each case, a carbohydrate based wound covering such as those using cotton, hyaluronic acid, and the like can covalently couple the pH indicator directly into the carbohydrate fiber thereby avoiding leaching of the indicator. Likewise, protein based therapeutics such as those incorporating, e.g., collagen can likewise incorporate into the polymer.

The various polymerizable groups can also attach to nucleic acids such as DNA and RNA, including siRNA, providing nucleic acid probes.

In addition to the above, when multiple polymerizable groups are employed in the same molecule, the molecule can be used both as a cross-linking agent as well as a pH indicator thereby obviating the need for all or some of a separate cross-linking agent if the polymer is to be cross-linked.

The invention claimed is:
1. A compound of Formula (I-C):

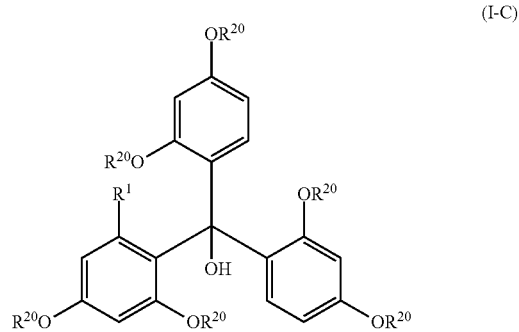

(I-C)

wherein
R¹ is hydrogen or —OR²⁰;
each R²⁰ independently is methyl, vinyl, allyl, —(CH₂)ₘ—OCOCH=CH₂, or —(CH₂)ₘ—OCOC(Me)=CH₂, provided that at least one R²⁰ is not methyl; and m is 2-10.
2. The compound of claim 1, wherein 1, 2, or 3 R²⁰ groups are —(CH₂)ₘ—OCOC(Me)=CH₂.

* * * * *